United States Patent [19]

Carter et al.

[11] Patent Number: 4,968,493

[45] Date of Patent: * Nov. 6, 1990

[54] METHOD FOR CONTROLLING CHRONIC RESPIRATORY DISEASE, FOWL CHOLERA AND NECROTIC ENTERITIS IN AVIAN SPECIES

[75] Inventors: Guy T. Carter; Michael Greenstein, both of Suffern; Joseph J. Goodman, Spring Valley; Donald B. Borders, Suffern, all of N.Y.; William M. Maiese, Bridgewater, N.J.; Raymond T. Testa, Cedar Grove, N.J.

[73] Assignee: American Cyanamid Company, Stamford, Conn.

[*] Notice: The portion of the term of this patent subsequent to Nov. 10, 2004 has been disclaimed.

[21] Appl. No.: 371,666

[22] Filed: Jun. 19, 1989

Related U.S. Application Data

[63] Continuation of Ser. No. 114,900, Oct. 29, 1987, abandoned, which is a continuation-in-part of Ser. No. 880,230, Jun. 30, 1986, Pat. No. 4,705,688.

[51] Int. Cl.$^5$ .............................................. A61K 35/74
[52] U.S. Cl. ..................................................... 424/122
[58] Field of Search ........................................ 424/122

Primary Examiner—Jerome D. Goldberg
Attorney, Agent, or Firm—Alice C. Brennan

[57] ABSTRACT

This invention provides a method for treating chronic respiratory disease, fowl cholera and necrotic enteritis in infected birds, by orally administering thereto a pharmaceutically effective amount of antibiotic LL-E19020α, antibiotic LL-E19020β or a physiologically acceptable salt thereof.

8 Claims, 8 Drawing Sheets

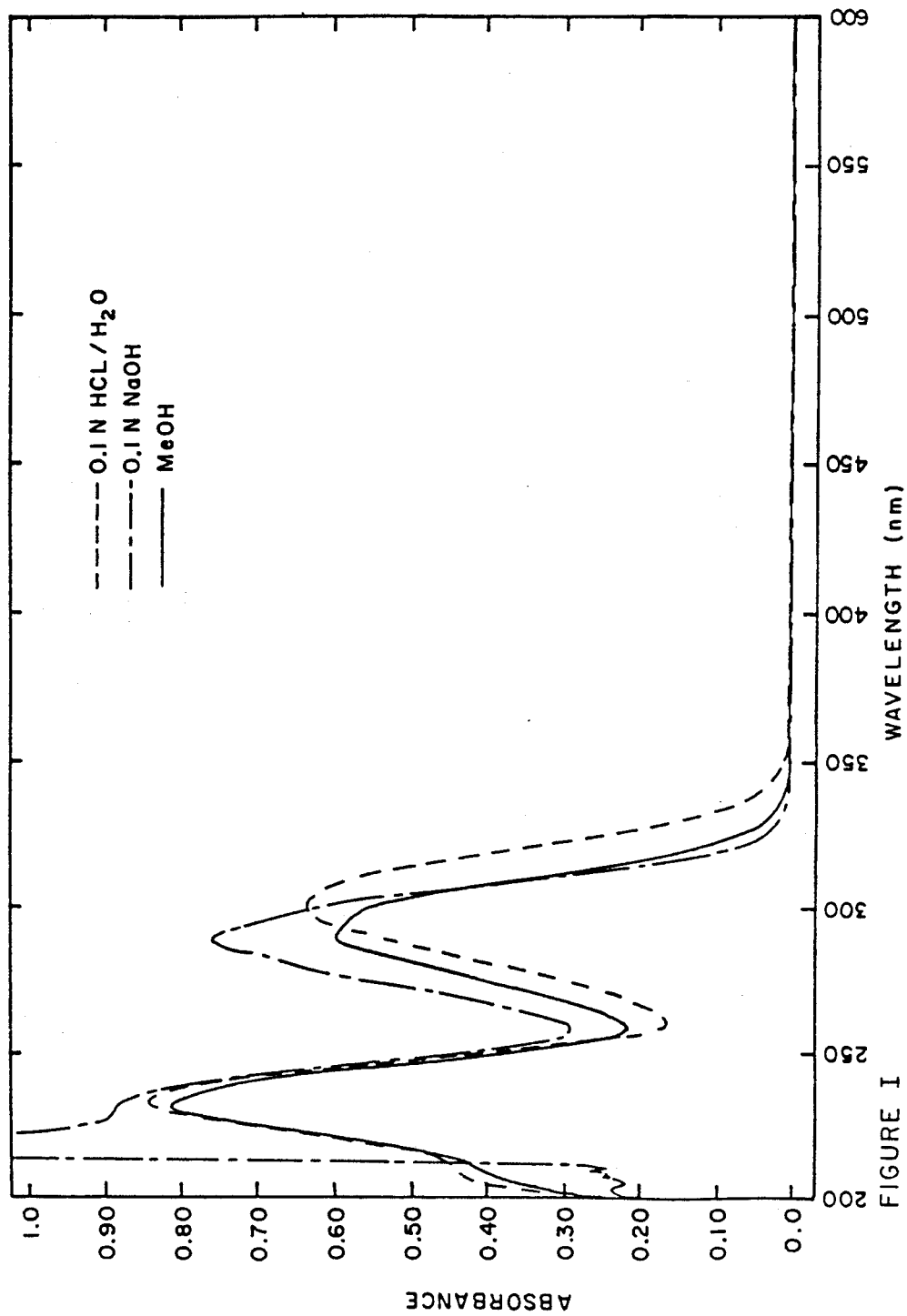
FIGURE I

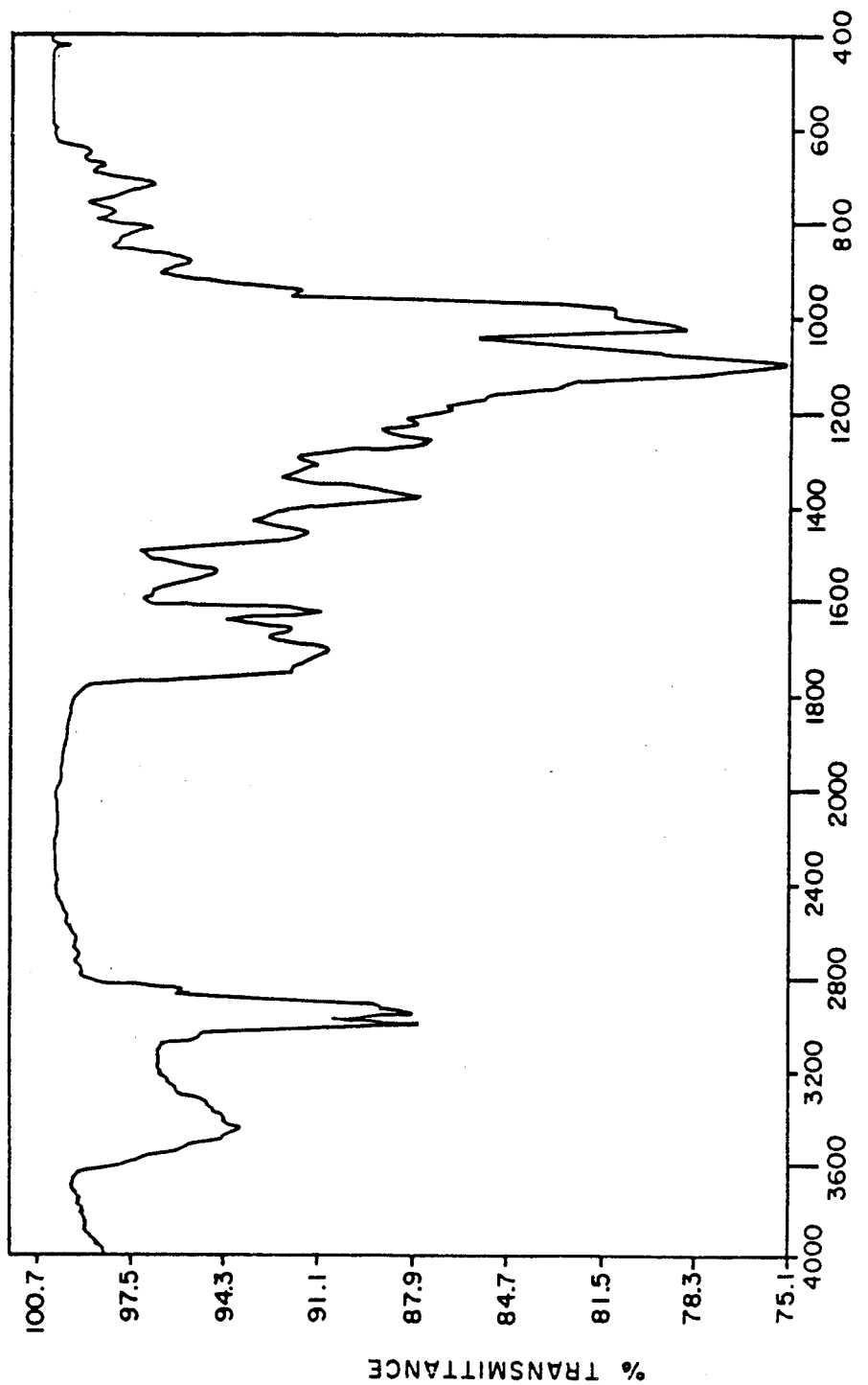
FIGURE II

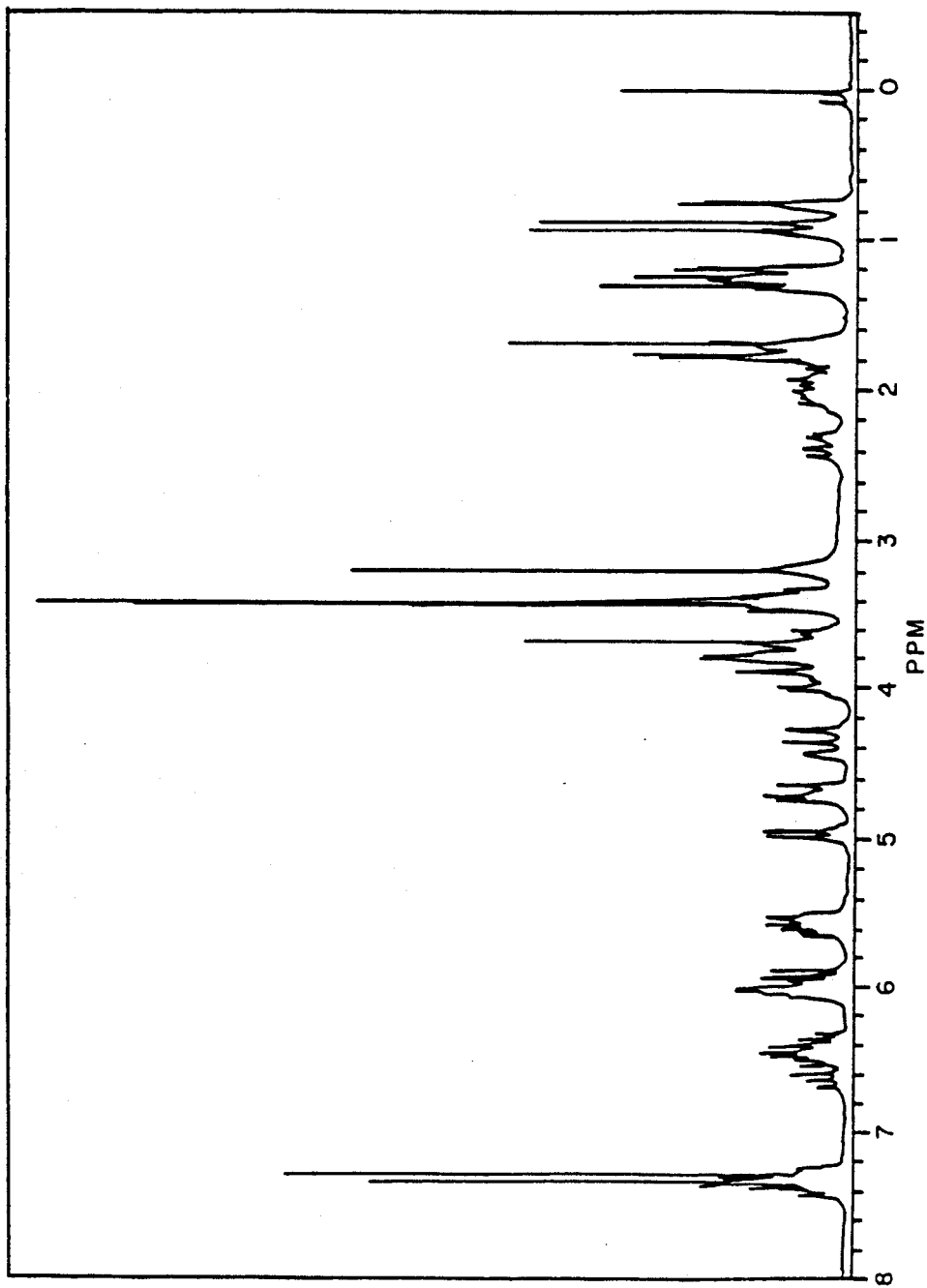
FIGURE III

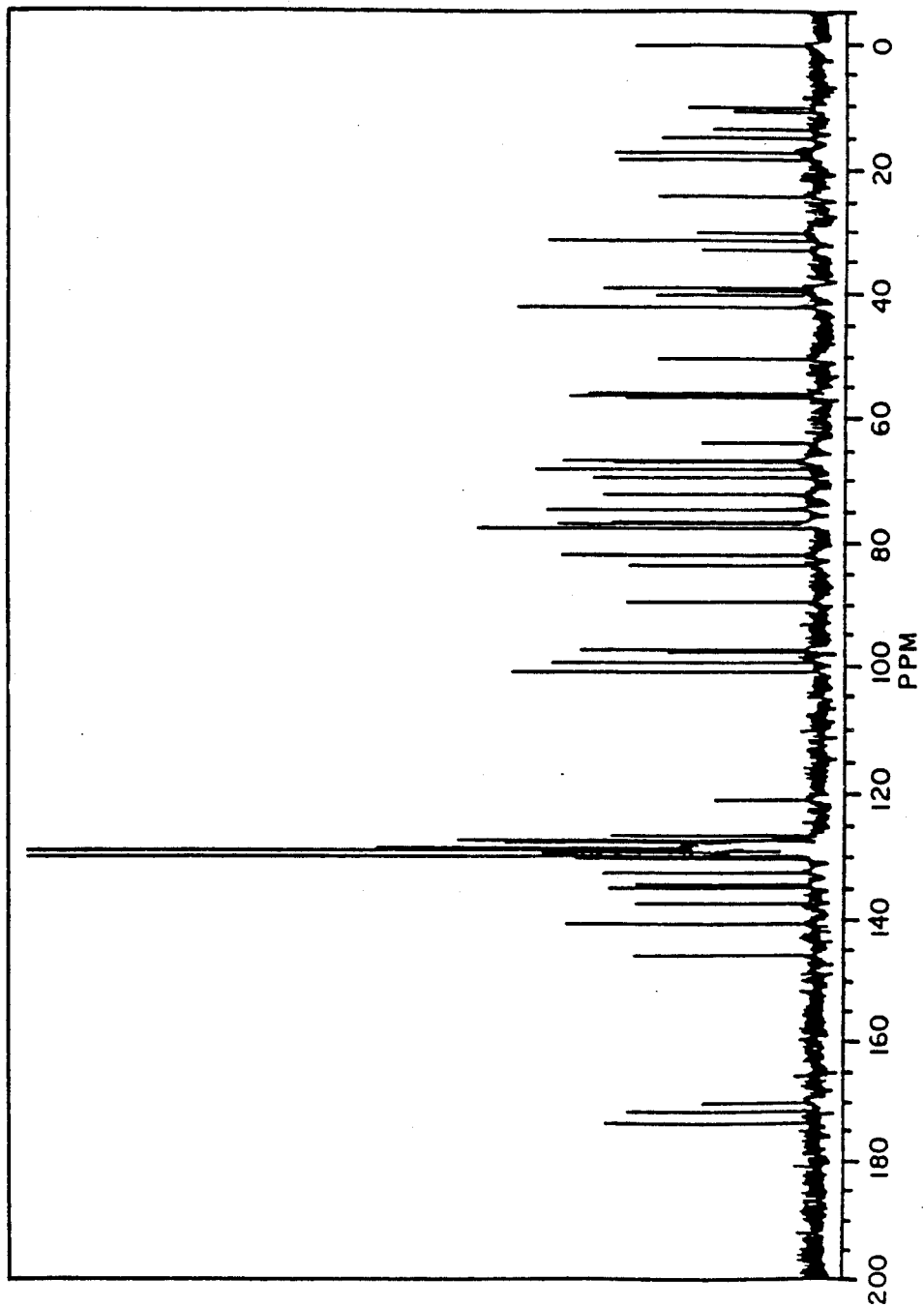
FIGURE IV

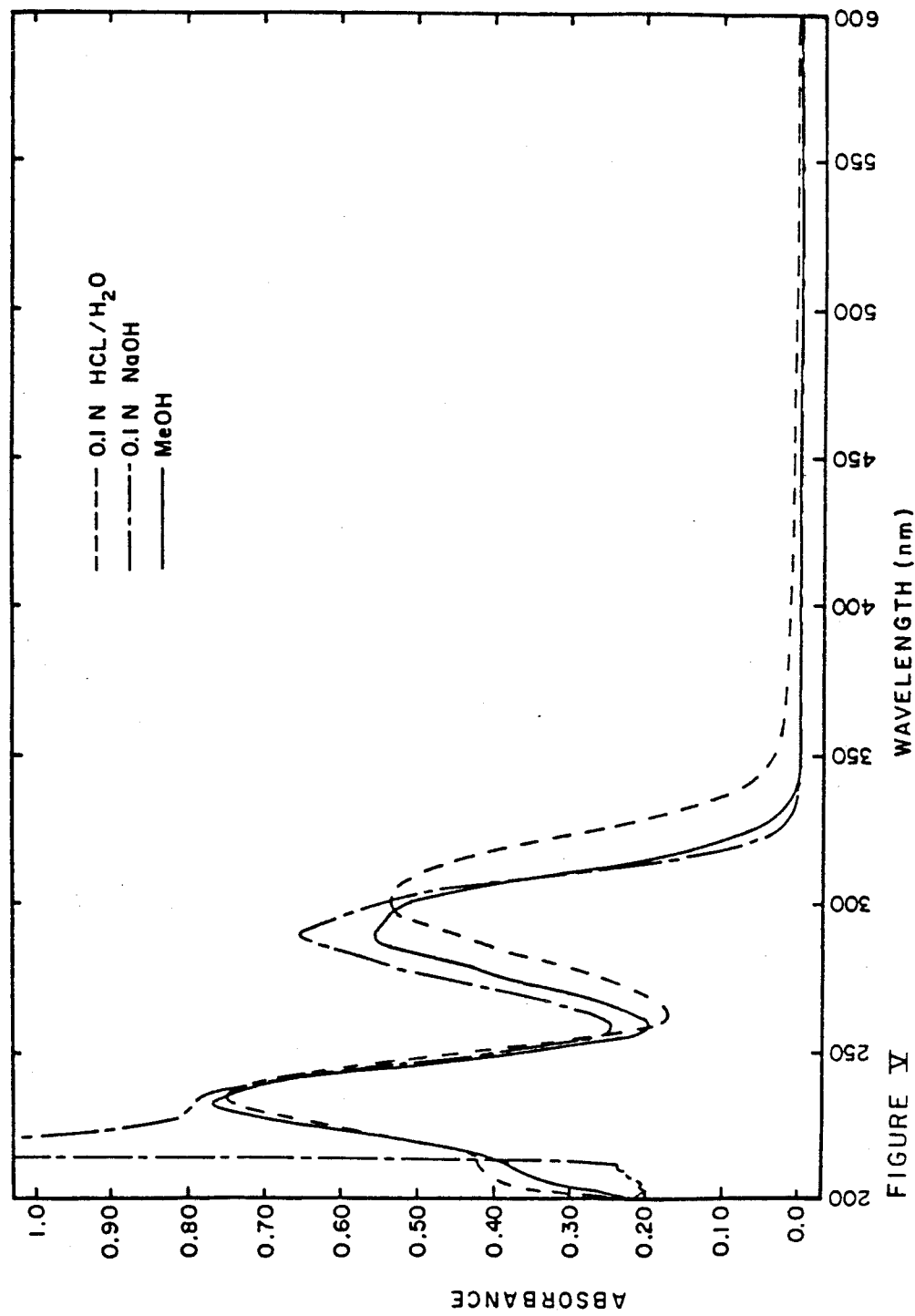

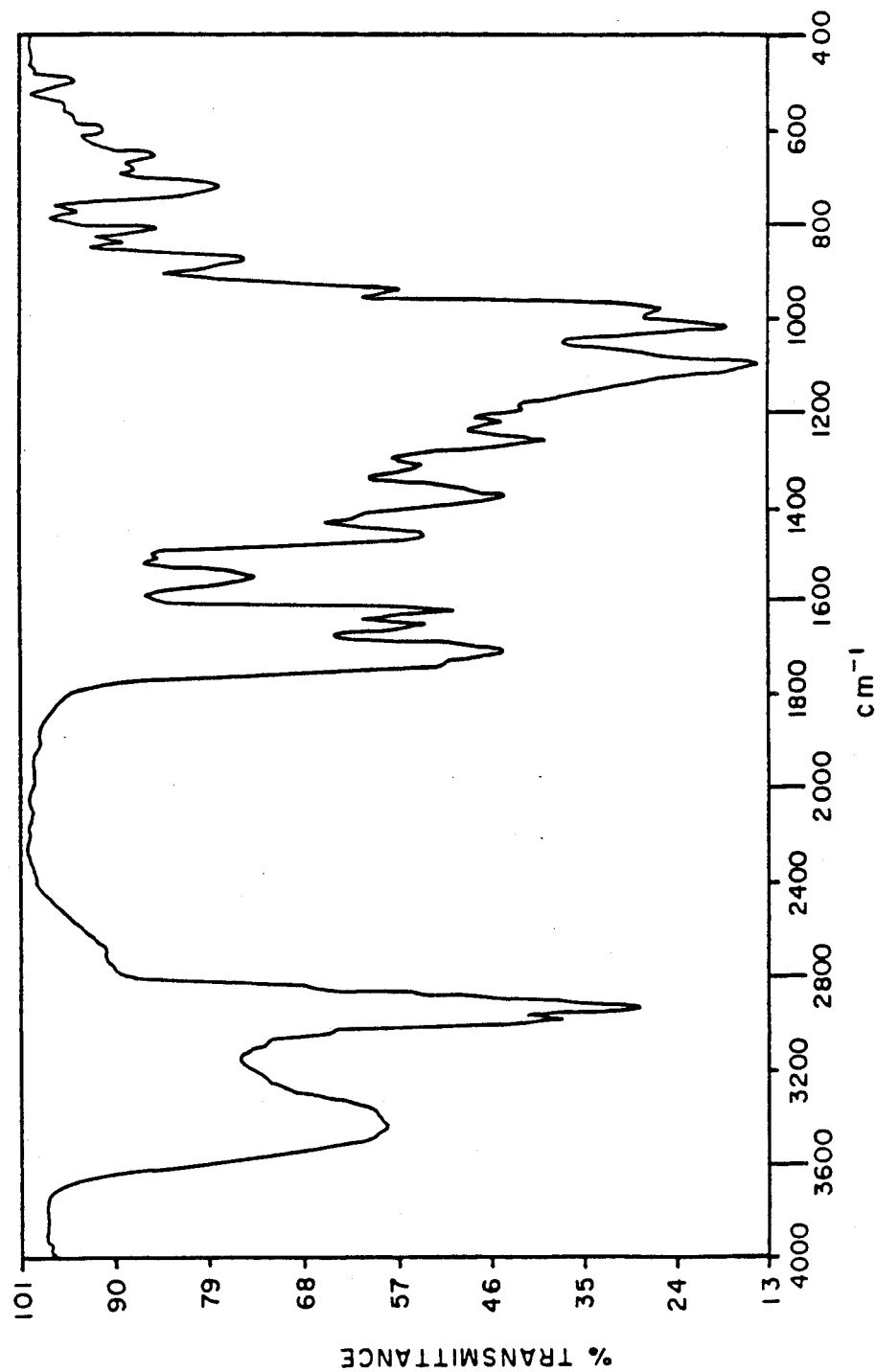
FIGURE VI

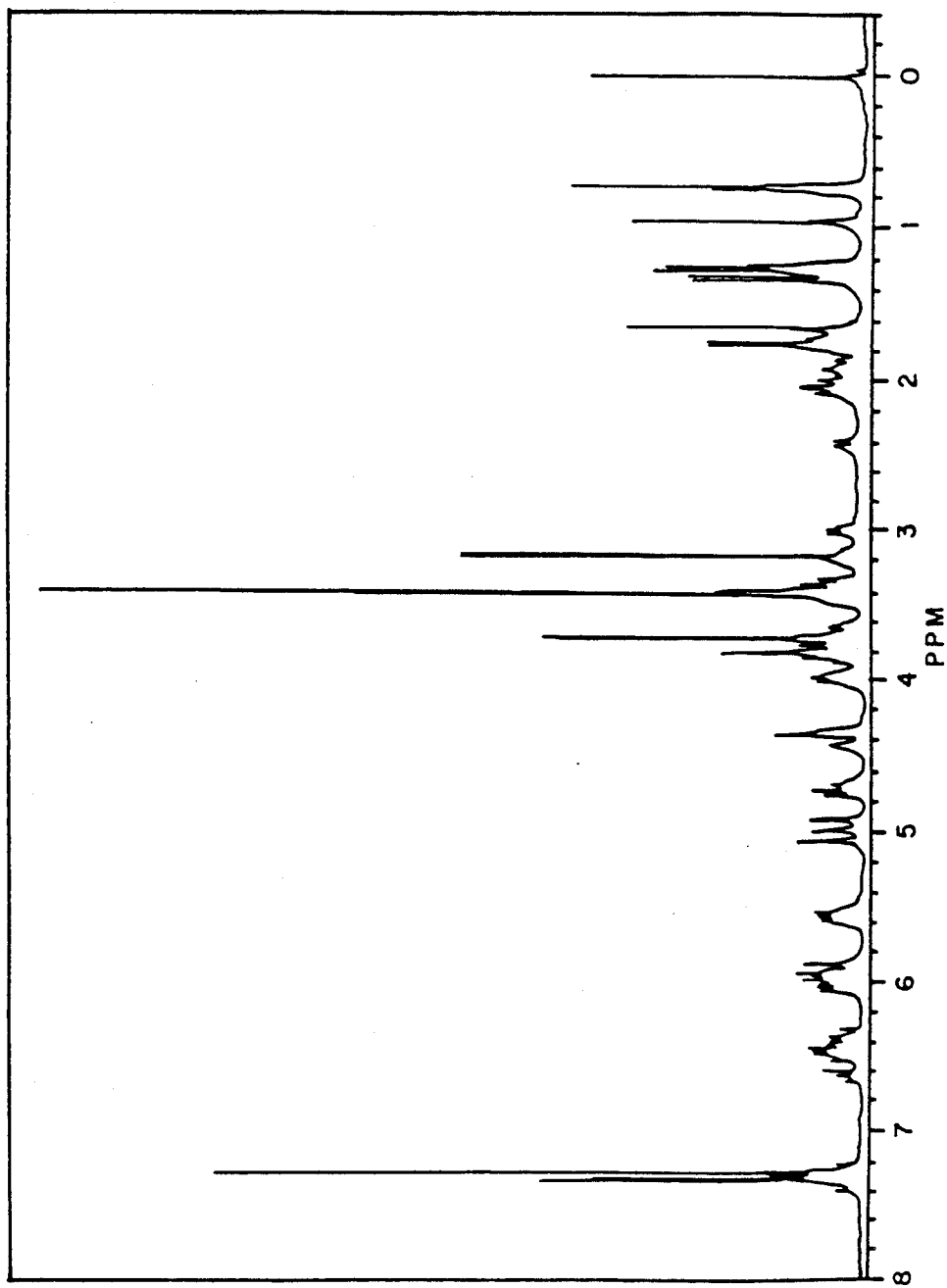
FIGURE VII

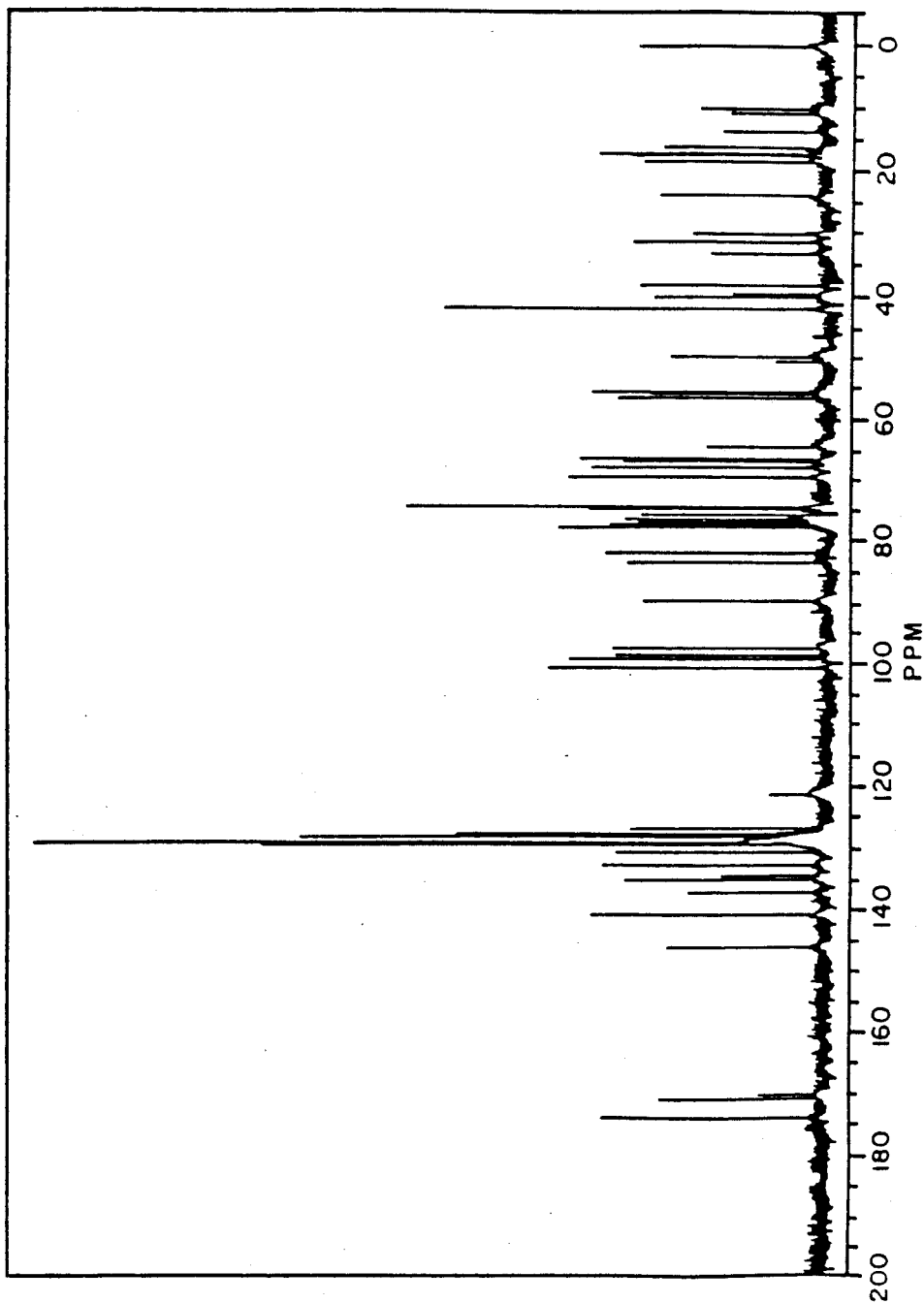
FIGURE VIII

METHOD FOR CONTROLLING CHRONIC RESPIRATORY DISEASE, FOWL CHOLERA AND NECROTIC ENTERITIS IN AVIAN SPECIES

This application is a continuation, of appliication Ser. No. 114,900, filed Oct. 29, 1987, now abandoned which is a continuation-in-part of U.S. application Ser. No. 880,230, filed June 30, 1986, now U.S. Pat. No. 4,705,688.

SUMMARY OF THE INVENTION

This invention relates to a method of treating birds infected with a causative agent for necrotic enteritis, chronic respiratory disease or fowl cholera, to reduce and/or eliminate the infections in said birds. More particularly, the invention relates to a method for orally administering to poultry, game birds raised in captivity, avian pets or avian zoological specimens infected with *Clostridium perfringes, Mycoplasma gallisepticum* or *Pasturella multocida*, a pharmaceutically effective amount of antibiotic LL-E19020α, antibiotic LL-E19020β or a physiologically acceptable salt thereof, to reduce and/or eliminate these infections in said birds.

BRIEF DESCRIPTION OF THE DRAWINGS

FIG. I shows ultraviolet absorption spectra of LL-E19020α.

FIG. II shows an infrared absorption spectrum of LL-E19020α.

FIG. III shows a proton nuclear magnetic resonance spectrum of LL-E19020α.

FIG. IV shows a carbon-13 nuclear magnetic resonance spectrum of LL-E19020α.

FIG. V shows ultraviolet absorption spectra of LL-E19020β.

FIG. VI shows an infrared absorption spectrum of LL-E19020β.

FIG. VII shows a proton nuclear magnetic resonance spectrum of LL-E19020β.

FIG. VIII shows a carbon-13 nuclear magnetic resonance spectrum of LL-E19020β.

DESCRIPTION OF THE PREFERRED EMBODIMENTS

The structures of antibiotics LL-E19020α and β have not been elucidated but they are described below in conjunction with their physico-chemical characteristics:

The physico-chemical characteristics of LL-E19020α are as follows:

LL-E19020α

1. Approximate elemental analysis: C 62.73; H 7.60; N 1.00; O 28.67 (by difference);
2. Molecular weight: 1225 (FABMS);
3. Apparent molecular formula: $C_{65}H_{95}NO_{21}$;
4. Specific rotation: $[\alpha]_D^{26} = O$ (C 0.385, methanol);
5. Ultraviolet absorption spectra: as shown in FIG. I

| | |
|---|---|
| $UV_{MAX}^{CH_3OH} =$ | 233 nm (ε 49,800) |
| | 290 nm (ε 36,600) |
| $UV_{MAX}^{0.1N\ HCl} =$ | 234 nm (ε 51,500) |
| | 300 nm (ε 38,900) |
| $UV_{MAX}^{0.1N\ NaOH} =$ | 217 nm (ε 82,700) |
| | 290 nm (ε 45,900) |

6. Infrared absorption spectrum: as shown in FIG. II (KBr disc): 3420, 2970, 2925, 1717, 1695, 1647, 1617, 1525, 1445, 1365, 1092, 1018 cm$^{-1}$;
7. Proton nuclear magnetic resonance spectrum: as shown in FIG. III (300 MHz, CDCl$_3$);
8. Carbon-13-nuclear magnetic resonance spectrum: as shown in FIG. IV (75 MHz, CDCl$_3$, ppm downfield from TMS), significant peaks as listed below;

| | | | | | |
|---|---|---|---|---|---|
| 173.3 | 129.0 | 97.3 | 74.2 | 55.4 | 17.2 |
| 171.4 | 128.6(2x) | 97.0 | 72.0 | 49.8 | 17.0 |
| 170.1 | 128.43 | 89.2 | 71.9 | 41.8(2x) | 14.8 |
| 145.7 | 128.38 | 83.3 | 69.1 | 39.8 | 13.5 |
| 140.3 | 128.1(2x) | 81.6 | 67.5 | 39.1 | 10.8 |
| 137.0 | 127.5 | 77.6 | 66.4 | 38.8 | 10.0 |
| 134.4 | 127.1 | 77.0 | 66.1 | 32.9 | |
| 133.9 | 126.3 | 76.4 | 63.5 | 31.0 | |
| 132.0 | 120.8 | 74.6 | 56.5 | 29.9 | |
| 130.1 | 100.6 | 74.5 | 56.0 | 23.8 | |
| 129.5(2x) | 99.0 | 74.4 | 55.6 | 18.1 | |

2x = two overlapping signals

LL-E19020β

1. Approximate elemental analysis: C 63.33; H 7.72; N 1.16; O 27.79 (by difference);
2. Molecular weight: 1225 (FABMS);
3. Apparent molecular formula: $C_{65}H_{95}NO_{21}$;
4. Specific rotation: $[\alpha]_D^{26} = -17 \pm 2$ (C 0.445, methanol);
5. Ultraviolet absorption spectra: as shown in FIG. V

| | |
|---|---|
| $UV_{MAX}^{CH_3OH} =$ | 233 nm (ε 47,000) |
| | 290 nm (ε 34,100) |
| $UV_{MAX}^{0.1N\ HCl} =$ | 234 nm (ε 46,600) |
| | 301 nm (ε 32,800) |
| $UV_{MAX}^{0.1N\ NaOH} =$ | 217 nm (ε 77,800) |
| | 290 nm (ε 39,700) |

6. Infrared absorption specturm: as shown in FIG. VI (KBr disc): 3430, 2970, 2930, 1712, 1648, 1620, 1543, 1454, 1367, 1265, 1098, 1020, 980 cm$^{-1}$;
7. Proton nuclear magnetic resonance specturm: as shown in FIG. VII (300 MHZ, CDCl$_3$);
8. Carbon-13 nuclear magnetic resonance spectum, as shown in FIGS. VIII (75 MHz, CDCl$_3$, ppm downfield TMS), significant peaks as listed below:

| | | |
|---|---|---|
| 173.6 | 99.0 | 55.4 |
| 170.6 | 98.4 | 49.6 |
| 170.0 | 97.2 | 41.6(2x) |
| 145.6 | 89.2 | 39.8 |
| 140.2 | 83.3 | 39.1 |
| 136.7 | 81.6 | 38.0 |
| 134.4 | 77.6 | 32.9 |
| 133.9 | 77.5 | 31.1 |
| 132.0 | 76.2 | 29.9 |
| 130.1 | 75.5 | 23.7 |
| 129.1(2x) | 74.6 | 18.1 |
| 128.9 | 74.5 | 17.2 |
| 128.6(2x) | 74.2(2x) | 17.0 |
| 128.5 | 69.1 | 16.2 |
| 128.4 | 68.9 | 13.5 |
| 128.3 | 67.5 | 10.8 |
| 128.2 | 66.6 | 10.0 |
| 127.8 | 66.1 | |
| 127.2 | 64.1 | |
| 126.5 | 56.5 | |
| 120.9 | 56.0 | |

| | |
|---|---|
| 100.6 | 55.6 |

2x = two overlapping signals

The new antibacterial agents LL-E19020α and LL-E19020β are formed during the cultivation under controlled conditions of a new strain of *Streptomyces lydicus* ssp. *tanzanius*.

This microorganism is maintained in the culture collection of the Medical Research Division, American Cyanamid Company, Pearl River, NY as culture number LL-E19020. A viable culture of this new microorganism has been deposited with the Patent Culture Collection Laboratory, Northern Regional Research Center, U.S. Department of Agriculture, Peoria, Illinois 61604, and has been added to its permanent collection. It has been assigned the strain designation NRRL 18036 by said depository. Access to said culture, under strain designation NRRL 18036, during pendency of the instant application shall be available to one determined by the Commissioner of Patents and Trademarks to be entitled thereto under 37 C.F.R. §1.14 and 35 U.S.C. §122, and all restrictions on availability to the public of such culture will be irrevocably removed upon grant of a patent on the instant application.

Culture LL-E19020 was isolated from a soil sample taken in a pasture near Lake Manyara, Tanzania, Africa.

Culture LL-E19020 produces short spiral spore chains, 10–50 spores long, with occasional longer chains. These tend to coalesce to form dry blackish masses on such ISP media as oatmeal and inorganic salts-starch. The spores have smooth surfaces as assessed by electron microscopy. The strain contains the L isomer of diaminopimelic acid, and may thus be assigned to the genus *Streptomyces*.

In the ISP tests for utilization of carbohydrates, LL-E19020 shows growth on arabinose, fructose, inositol, mannitol, raffinose, rhamnose, sucrose and xylose. Cellulose is not utilized.

The reactions of LL-E19020 in the Gordon physiological series are compared in the following Table I with those of *Streptomyces lydicus* ISP 5461 which it most closely resembles morphologically and physiologically.

Because LL-E19020 differs from ISP 5461 in five characteristics (xanthine hydrolysis, decarboxylation of oxalate, acid from erythritol, rhamnose and β-methyl-D-xyloside) it is designated as a subspecies of *Streptomyces lydicus*.

TABLE I

| Gordon Test Reactions of LL-E19020 and *Streptomyces lydicus* ISP 5461 | | |
|---|---|---|
| Reaction | LL-E19020 | ISP 5461 |
| Degradation/Transformation of | | |
| Casein | + | + |
| Xanthine | − | + |
| Hypoxanthine | + | + |
| Tyrosine | + | + |
| Adenine | + | + |
| Production of | | |
| Amylae | + | + |
| Gelatinase | + | + |
| Phosphatase | + | + |
| Nitrate Reductase | − | − |
| Urease | + | + |
| Esculinase | + | + |

TABLE I-continued

| Gordon Test Reactions of LL-E19020 and *Streptomyces lydicus* ISP 5461 | | |
|---|---|---|
| Reaction | LL-E19020 | ISP 5461 |
| Growth on/in | | |
| 5% Sodium chloride | + | + |
| Salicylate | − | − |
| Lysozyme Broth | trace | trace |
| Utilization of | | |
| Actate | + | + |
| Benzoate | − | − |
| Citrate | + | + |
| Lactate | + | + |
| Malate | + | + |
| Mucate | + | + |
| Oxalate | + | − |
| Propionate | + | + |
| Pyruvate | + | + |
| Succinate | + | + |
| Tartrate | − | − |
| Growth at | | |
| 10° C. | + | + |
| 42° C. | − | − |
| 50° C. | − | − |
| Acid from | | |
| Adonitol | + | + |
| Arabinose | + | + |
| Cellobiose | + | + |
| Dextrin | + | + |
| Dulcitol | − | − |
| Erythritol | + | − |
| Fructose | + | + |
| Galctose | + | + |
| Glucose | + | + |
| Glycerol | + | + |
| Inositol | + | + |
| Lactose | + | + |
| Maltose | + | + |
| Mannitol | + | + |
| Mannose | + | + |
| Melibiose | + | + |
| α-Methyl-D-Glucoside | + | + |
| Raffinose | + | + |
| Rhamnose | + | − |
| Salicin | + | + |
| Sorbitol | + | + |
| Sucrose | + | + |
| Trehalose | + | + |
| Xylose | + | + |
| β-Methyl-D-Xyloside | + | − |

It is to be understood that for the production of these new antibacterial agents the present invention is not limited to this particular organism or to organisms fully answering the above characteristics which are given for illustrative purposes only. In fact, it is desired and intended to include the use of mutants produced from this organism by various means such as exposure to X-radiation, ultraviolet radiation, N'-methyl-N'-nitro-N-nitrosoguanidine, actinophages and the like.

The in vitro antibacterial activity of LL-E19020α and β was determined against a spectrum of gram-positive and gram-negative bacteria by a standard agar dilution method. Mueller-Hinton agar containing 5% sheep blood and two-fold decreasing concentrations of either LL-E19020α or β were poured into petri dishes. The agar surfaces were inoculated with 1 to $5 \times 10^4$ colony forming units of bacteria by means of the Steers replicating device. The lowest concentration of antibiotic that inhibited growth of a bacterial strain after 18 hours incubation was recorded as the minimal inhibitory concentration for that strain. The results are given in Table II.

TABLE II

*In vitro* Antibacterial Activity of LL-E19020α and β

| Organism | | Minimal Inhibitory Concentration (mcg/ml) | |
|---|---|---|---|
| | | LL-E19020α | LL-E19020β |
| *Staphylococcus aureus* | ATCC 25923 | >256 | >256 |
| *Staphylococcus aureus* | Smith | 128 | >128 |
| *Staphylococcus aureus* | VGH-84-45 | >256 | >128 |
| *Staphylococcus aureus* | CMC-83-127 | >256 | >128 |
| *Staphylococcus aureus* | CMC-83-131 | >256 | >128 |
| *Staphylococcus aureus* | CMC-83-132 | >256 | >128 |
| *Staphylococcus aureus* | SSC-82-57 | >256 | >128 |
| *Staphylococcus epidermidis* | IO-83-58 | >256 | >128 |
| *Staphylococcus saprophyticus* | VGH-84-50 | >256 | >128 |
| *Streptococcus sp.* (β-hemolytic) | C203 | 0.5 | 0.5 |
| *Streptococcus sp.* (β-hemolytic) | VGH-84-60 | 0.25 | 0.25 |
| *Streptococcus sp.* (β-hemolytic) | VGH-84-61 | 1 | 0.5 |
| *Streptococcus sp.* (β-hemolytic) | VGH-84-62 | 1 | 0.5 |
| *Streptococcus sp.* (β-hemolytic) | VGH-84-63 | 0.12 | 0.12 |
| *Streptococcus sp.* (β-hemolytic) | VGH-84-64 | 0.12 | 0.12 |
| *Streptococcus pneumoniae* | SVI | 1 | 1 |
| *Streptococcus pneumoniae* | K-84-21 | 1 | 0.5 |
| *Streptococcus pneumoniae* | VGH-84-56 | 1 | 0.5 |
| *Streptococcus pneumoniae* | VGH-84-57 | 2 | 1 |
| *Streptococcus pneumoniae* | VGH-84-58 | 0.25 | 0.25 |
| *Streptococcus pneumoniae* | VGH-84-59 | 0.25 | 0.25 |
| *Enterococcus* | VGH-84-65 | 256 | >128 |
| *Enterococcus* | VGH-84-68 | >256 | >128 |
| *Enterococcus* | IO-83-28 | >256 | >128 |
| *Enterococcus* | IO-83-40 | >256 | >128 |
| *Enterococcus* | CMC-83-72 | >256 | >128 |
| *Escherichia coli* | 311 | >256 | >128 |
| *Klebsiella pneumoniae* | AD | >256 | >128 |
| *Enterobacter cloacae* | VGH-84-37 | >256 | >128 |
| *Morganella morganii* | VGH-84-71 | >256 | >128 |
| *Serratia marcescens* | K-84-18 | >256 | >128 |
| *Pseudomonas aeruginosa* | 12-4-4 | >256 | >128 |
| *Bacteroides fragilis* | NYC 77-1 | >128 | >128 |
| *Clostridium difficile* | ATCC 17858 | 4 | 1 |
| *Clostridium perfringens* | ATCC 13124 | 16 | 4 |
| *Peptococcus magnus* | ATCC 29328 | 0.12 | 0.5 |
| *Peptococcus magnus* | ATCC 14956 | 0.12 | 0.5 |

The in vivo antibacterial activity of antibiotics LL-E19020α and β was established by infecting female CD-1 mice from Charles River Laboratories, weighing 20±2 g each, intraperitoneally with either 1.7×10$^2$CFU/0.5 ml of broth of *Streptococcus pyogenes* C203 or 6.5×10$^5$ CFU/0.5 ml of broth of *Staphylococcus aureus* Smith. The mice were treated subcutaneously, 30 minutes before infection with the indicated dose of the test compound in 0.5 ml of 0.2% aqueous agar. The results of this test appear in Table III.

TABLE III

In vivo Activity of LL-E19020α and β

| Single Subcutaneous Dose (mg/kg) | Survival Ratios 7 Days After Infection | | | |
|---|---|---|---|---|
| | *S. pyogenes* C203 | | *S. aureus* Smith | |
| | LL-E19020α | LL-E19020β | LL-E19020α | LL-E19020β |
| 256 | NT | NT | 3/5 | 1/5 |
| 64 | 5/5 | 5/5 | 3/5 | 1/5 |
| 32 | 5/5 | 5/5 | NT | NT |
| 16 | 5/5 | 5/5 | 3/5 | 1/5 |
| 8 | 4/5 | 3/5 | NT | NT |
| 4 | 2/5 | 2/5 | 2/5 | 1/5 |
| Non-treated infected controls | 0/10 | 0/10 | 0/10 | 0/10 |

NT = not tested

Antibiotics LL-E19020α and LL-E19020β derive their utility from their antibacterial activity. For example, these antibiotics may be used in the suppression of bacterial infections as a topical antibacterial agents and as general disinfectants for laboratories.

Surprisingly, we have also found that these antibiotics are useful for treating bacterial infections in avian species. In particular, the above-said antibiotics are useful for reducing or eliminating necrotic enteritis, chronic respiratory disease and fowl cholera from infected birds.

In accordance with this invention we find that successful treatment of infected birds can generally be achieved by the oral administration of LL-E19020α, LL-E19020β or a physiologically acceptable salt thereof, in or with the feed or drinking water of said-infected birds. Usually about 0.5 ppm to 1000 ppm and preferably about 1.0 ppm to 50 ppm of LL-E19020α, LL-E19020β or the physiologically acceptable salt thereof is effective for reducing or eliminating the infection in the birds.

In addition, we now find that antibiotics LL-E19020α, LL-E19020β or physiologically acceptable salts thereof, may be orally administered at pharmaceutically effective levels to birds infected with *Clostridium perfringens, Mycoplasma gallisepticum* or *Pasturella multocida*, to reduce or eliminate these infections in said birds.

The above-said pathogens are the causative agents for necrotic enteritis, chronic respiratory disease and fowl cholera; diseases that continually plague the poultry industry and are annually responsible for multi-million dollar losses to poultry growers and egg producers.

While major economic losses from these diseases generally occur in poultry such as chickens, turkeys, geese and ducks, it has now been established that these diseases also occur in game birds raised in captivity, such as quail and pheasants, in waterfowl and birds of prey maintained in zoological gardens and in exotic and feral birds kept as companions or pets. It is therefore an object of this invention to provide a method for treating birds infected with the causative agents for necrotic enteritis, chronic respiratory disease or fowl cholera to reduce or eliminate the infections in said birds.

General Fermentation Conditions

Cultivation of *Streptomyces lydicus* ssp. *tanzanius* NRRL 18036 may be carried out in a wide variety of liquid culture media. Media which are useful for the production of LL-E19020α and LL-E19020β include an assimilable source of carbon, such as dextrin, sucrose, molasses, glycerol, etc; an assimilable source of nitrogen such as protein, protein hydrolysate, polypeptides, amino acids, corn steep liquor, etc; and inorganic anions and cations, such as potassium, sodium, ammonium, calcium, sulfate, carbonate, phosphate, chloride, etc. Trace elements such as boron, molybdenum, copper, etc., are supplied as impurities of other constituents of the media. Aeration in tanks and bottles is supplied by forcing sterile air through or onto the surface of the fermenting medium. Further agitation in tanks is provided by a mechanical impeller. As antifoam agent such as silicon oil may be added as needed.

General Procedure for the Isolation of LL-E19020α and β

The LL-E19020α and LL-E19020β are recovered from the fermentation broth by pH adjustment to 4.5–5.5, filtration through diatomaceous earth, extraction into a solvent such as ethyl acetate, concentration, dissolution in a solvent such as dichloromethane and purification by column chromatography on silica gel using successively, dichloromethane and methanol:dichloromethane (1:4), giving a crude product.

The crude product is then separated into the α and β components and further purified by high performance liquid chromatography on a reverse-phase column using the system acetonitrile, 0.1M ammonium acetate buffer pH 4.3 (1:1).

The invention will be further described in conjunction with the following non-limiting examples.

EXAMPLE 1

Inoculum Preparation

A typical medium used to grow the primary inoculum was prepared according to the following formula

| | |
|---|---|
| Dextrose | 1.0% |
| Dextrin | 2.0% |
| Yeast extract | 0.5% |
| NZ Amine A ®[1] | 0.5% |
| Calcium carbonate | 0.1% |
| Water qs | 100.0% |

[1][A pancreatic digest of casein registered trademark of Sheffield Chemical, Norwich, NY]

This medium was adjusted to pH 7.0 and then sterilized. A 100 ml portion of this sterile medium in a 500 ml flask, was inoculated with mycelial scrapings from an agar slant of *Streptomyces lydicus* ssp. *tanzanius* NRRL 18036. The medium was then placed on a rotary shaker and incubated at 28° C. for 48 hours. This primary inoculum was then used to inoculate 10 liters of the same sterile medium in a bottle. This medium was grown for 24 hours providing secondary inoculum. This secondary inoculum was then used to inoculate 250 liters of the same sterile medium in a tank. This medium was grown at 28° C. for 48 hours with a sterile air flow of 200 liters per liter of mash per minute and agitation by an impeller driven at 220 rpm, providing tertiary inoculum.

EXAMPLE 2

Fermentation

A fermentation medium of the following formulation was prepared

| | |
|---|---|
| Dextrin | 3.0% |
| Molasses | 2.0% |
| Soy peptone | 0.75% |
| Yeast extract | 0.25% |
| Calcium carbonate | 0.25% |
| Water qs | 100.0% |

This medium was sterilized and 2700 liters was then inoculated with 300 liters of tertiary inoculum from Example 1. The fermentation was conducted at 28° C., with a sterile air flow of 0.55 liters of air per liter of mash per minute and agitation by an impeller driven at 100 rpm for 113 hours, at which time the mash was harvested.

EXAMPLE 3

Isolation and Purification of LL-E19020α and β

The harvest mash from two fermentations conducted as described in Example 2 were combined, making a total of 6000 liters, adjusted to pH 5 with hydrochloric acid and filtered through diatomaceous earth. The filtrate was extracted with ethyl acetate and the extract concentrated to a syrup.

This syrup was dissolved in dichloromethane and applied to 1000 g of silica (60-200 mesh) on a sintered glass funnel. The silica column was first eluted with dichloromethane, collecting four 2 liter fractions and then with methanol:dichloromethane (1:4) collecting a 4 liter fraction. This 4 liter fraction was evaporated to dryness, giving 120 g of residue. The residue was redissolved in 4 liters of dichloromethane and applied to 500 g of silica on a sintered glass funnel. The silica was eluted with methanol:dichloromethane (1:4) collecting 2 liter fractions. Fractions 1 and 2 were combined and evaporated, giving 99 g of crude LL-E19020α and β.

This crude product was dissolved in methanol and applied to a 12 liter reverse-phase column (C18 bonded phase 40 micron). The column was eluted with acetonitrile, 0.1M ammonium acetate buffer pH 4.3 (1:1) at a rate of 1.0 liter per minute. Thirteen 24 liter fractions were collected. Fraction 7 contained LL-F19020α and fractions 11-13 contained LL-E19020β.

The antibiotics were extracted from the mobile phase using dichloromethane followed by evaporation and freeze drying from t-butanol, giving 10 g of LL-E19020α and 14 g of LL-E19020β, both as white solids.

EXAMPLE 4

PASTEURELLA DISK TEST

Sterile paper disks (¼" in diameter) are soaked in a 2.5 mg/ml solution of test compound and dried in a 37° C. incubator overnight. Standard antibiotic control disks are prepared for testing along with the test compound disks. The dried disks are stored at 2°-4° C. until used. Two test organisms, *Pasteurella multocida* 31081B and *Pasteurella haemolytica* 30660, are cultured in brain heart infusion broth for 5 hours at 37° C. A 1:10 dilution of each culture is made in Mueller-hinton broth. Two hundred milliliters of Mueller-Hinton agar are seeded with 1 ml of the diluted culture and aseptically poured into 9 inch×9 inch bioassay plates manufactured by Nunc. Use of the 9"×9" plates permits the testing of 36 disks per plate. Approximately disks are applied to the seeded agar plates and incubated for 18-20 hours at 37° C. Zones of inhibition are recorded.

T. HYODYSENTERIAE DISK TEST

Sterile paper disks (¼" in diameter) are soaked in a 2.5 mg/ml solution of a test compound and dried in a 37° C. incubator overnight. Standard antibiotic control disks are prepared for testing along with the test compound disks. The dried disks are stored at 2°-4° C. until used. Two *T. hyo.* stains, B78 (ATCC 27164) and B204 (ATCC 31212), are cultured for 24 hours at 38° C. in Hungate culture tubes containing 5 ml brain heart infusion broth supplemented with 2% fetal calf serum (prepared anaerobically). Two hundred milliliters of trypticase soy agar, containing 5% defibrinated bovine blood, are seeded with 1 ml of culture and aseptically poured into 9"×9" bioassay plates manufactured by Nunc. Use of the 9"×9" plate permit the testing of 36 disks per plate. Appropriate disks are applied to the agar plates which are then incubated for 24-48 hours at 38° C. in an anaerobic chamber containing 80% nitrogen, 10% carbon dioxide, and 10% hydrogen until hemolysis is complete. Zones of inhibited hemolysis are recorded.

MINIMUM INHIBITORY CONCENTRATION PROCEDURE BY AGAR DILUTION

1. Serial two-flow dilutions of drug are prepared in Mueller-Hinton broth in a range of 2560 μg/ml–0.15 μg/ml plus a solvent control.

2. Two milliliters of drug dilution (10X) are added to sterile screwcap bottles to which 18 ml of Mueller-Hinton agar containing 5.6% defibrinated sheep blood is added. Final drug concentration ranges 256 μg/ml–0.015 μg/ml in agar containing 5% sheep blood.

3. A few isolated colonies of each test organism are inoculated into 5 ml trypticase soy broth or brain heart infusion broth. The cultures are shaken at 35° C. for 5 hours.

4. Each culture is diluted 1:50 ($10^{-1.7}$) in Mueller-Hinton broth and applied to agar plates using a Steers replicator. Control plates should be seeded last to ensure that viable organisms were present throughout the procedure. Inoculated agar plates are allowed to stand undisturbed until the inoculum spots are completely absorbed.

5. The plates are inverted and incubated at 35° C. for 18 hours without $CO_2$.

6. The minimum inhibitory concentration (MIC) is taken as the lowest concentration of antimicrobial agent at which complete inhibition occurs. A very fine, barely visible haze or a single colony is disregarded.

MIC TEST ORGANISMS

*Staphylococcus aureus* ATCC 25923
*Staphylococcus aureus* 52 "Smith strain"
*Staphylococcus aureus* 14 ATCC 6538P
*Staphylococcus aureus* 335 Mastitis isolate
*Staphylococcus aureus* 336 Mastitis isolate
*Staphylococcus aureus* 344 Mastitis isolate
*Staphylococcus aureus* Penicillin resistant
*Streptococcus pyogenes* ATCC 19615
*Streptococcus pyogenes* 41
*Streptococcus agalactiae* 341
*Streptococcus agalactiae* 342
*Streptococcus agalactiae* 343
*Streptococcus dysgalactiae* 340
*Streptococcus faecalis* 42 Dr. Juke's #8043
*Streptococcus uberis* Cornell Mastitis Center
*Escherichia coli* ATCC 25922
*Escherichia coli* 81
*Escherichia coli* 80-654 Tetracycline resistant
*Pasteurella multocida* 31081B (in vitro disk test strain)
*Pasteurella multocida* 80-2548 (in vivo mouse model strain)
*Pasteurella multocida* 31451
*Pasteurella multocida* 32301
*Pasteurella multocida* 30170B
*Pasteurella multocida* 80-5945
*Pasteurella haemolytica* 30660 (in vitro disk test strain)
*Pasteurella haemolytica* L-101 National Animal Disease Center
*Pasteurella haemolytica* 80-6744
*Salmonella choleraesuis* var. Kunzendorf I-3
*Salmonella choleraesuis* var. Kunzendorf 4
*Bordetella bronchiseptica* "B" strain
*Bordetella bronchiseptica* 11266
*Bordetella bronchiseptica* 31068B
*Bordetella bronchiseptica* 11948A

MINIMUM INHIBITORY CONCENTRATION ASSAY FOR *Mycloplasma gallisepticum*

1. Serial two-fold dilutions of drug stock solutions are prepared in mycoplasma broth in a concentration of 2560 μg/ml–0.015 μg/ml plus a solvent control. These concentrations are 10X the final test concentration.

2. A frozen (−80° C.) stock culture of *Mycoplasma gallisepticum* "R" strain is thawed and a 0.5 ml aliquot is inoculated into 5 ml of mycoplasma culture broth. At the same time, 0.1 ml is plated on to a mycoplasma agar plate as a purity check. Both cultures are incubated at 37° C. Growth in broth is indicated by a color change from red to yellow. Growth on agar is observed with the aid of a stereoscope.

3. The MIC assay is carried out in 96 well microtiter plates. To each test well, 25 μl of 10X drug solution is aliquoted. Appropriate solvent controls are also included.

4. The mycoplasma inoculum is prepared by transferring a positive broth culture to fresh medium using the ratio of 0.2 ml culture:5.0 ml medium. Large amounts of inoculum are prepared as needed using the formula above.

5. A 225 μl aliquot of previously inoculated mycoplasma broth is added to each test well and mixed. A plastic sealer tape is applied and a small hole is placed over the center of each test well using sterile 25 guage needles. To avoid well cross-contamination, needles are changed for each drug. Further, tape puncturing proceeds from lowest to highest concentration of drug. Final test concentration ranges from 256 μg/ml–0.0015 μg/ml with total volume of 250 μl. Wells containing 250 μl of inoculated medium only and uninoculated medium are added as further controls.

6. The assay plate is incubated at 37° C. until a broth color change from red to yellow first occurs uniformly throughout the test plate. The MIC value is recorded as the concentration at which the broth color (red) remains unchanged.

EXAMPLE 5

Evaluation of antibiotics LL-E19020α and LL-E19020β for treating poultry infected with *Clostridium perfringens*

In these tests, on day old broiler chicks are placed in battery brooders and raised under standard conditions with nonmedicated feed until 12 days of age. On day 12 the chicks are wing handed, weighed and placed in growing batteries in groups of 10 birds/pen. All treatments, including controls both infected and uninfected, are replicated 4 times.

On day 12 all birds in the infected control and in the treatment groups which are to receive 5 and 50 ppm of E19020α or E19020β are given a mild challenge of *Eimeria acervulina*

On days 14–18 (five consecutive days) all birds except those in the non-infected control group are given 5 ml of an overnight broth culture of *Clostridium perfringens* type C by gavage.

On day 19 all birds are weighed and 3 preselected birds from each group are sacrificed and necropsied. The degree of pathology of the intestinal tract is scored as follows:

0=No gross lesions

1=Thin-walled or friable small intestine

2=Focal necrosis and/or ulceration

3=Large patches of necrosis

4=Sever, extensive necrosis

The remaining birds are held for another 7 days at which time they are sacrificed, and measurements and data recorded.

DATA MEASUREMENTS AND RECORDS

Individual body weights are made on days 12, 19, and 26.

Feed consumption is measured on days 12–19, and 26.

Intestinal lesion scores on three birds per group are made on day 19.

Daily health observations for each pen are made on days 12–26.

Results obtained are reported below.

TABLE IV

ANTIBACTERIAL DATA FOR E19020 ALPHA & E19020 BETA
PRIMARY IN VITRO DISK DIFFUSION TEST

| | ZONE SIZE (mm) | | | |
|---|---|---|---|---|
| | E19020 ALPHA | E19020 BETA | CTC | TIAMULIN |
| *Pasteurella multocida* 31081B | 15 | 13 | 25 | N/T |
| *Pasteurella haemolytica* 30660 | 13 | 13 | 11 | N/T |
| *Treponema hyodysenteriae* B78 (ATCC 27164) | 0 | N/T | 45 | 67 |
| *Treponema hyodysenteriae* B204 (ATCC 31212) | 15 | 11 | 37 | 70 |

N/T = Not Tested

TABLE V

MINIMUM INHIBITORY CONCENTRATIONS BY AGAR DILUTION

| | MIC (μg/ml) | |
|---|---|---|
| | E19020 ALPHA | E19020 BETA |
| *Staphylococus aureus* (7) | ≧256 | 128–≧256 |
| *Streptococcus pyogenes* (2) | 2 | 2–4 |
| *Streptococcus agalactiae* (4) | 2–8 | 2–4 |
| *Streptococcus faecalis* (1) | 8 | 8 |
| *Streptococcus uberis* (1) | 8 | 4 |
| *Escherichia coli* (2) | ≧256 | ≧256 |
| *Salmonella choleraesuis* (2) | >256 | >256 |
| *Bordetella bronchiseptica* (4) | >256 | >256 |
| *Pasteurella multocida* (6) | 8–16 | 8–16 |
| *Pasteurella haemolytica* (3) | 16 | 16 |

NOTE:
Numbers in parentheses indicate the number of strains tested.

TABLE VI

MINIMUM INHIBITORY CONCENTRATION BY MICRODILUTION

| | MIC (μg/ml) | | | | | |
|---|---|---|---|---|---|---|
| | E19020 ALPHA | E19020 BETA | CARBADOX | TIAMULIN | CTC | TYLOSIN |
| *Treponema hyodysenteriae* B78 (ATCC 27164) | 1 | 1 | 0.5 | 0.015 | N/T | N/T |
| *Treponema hyodysenteriae* B204 (ATCC 31212) | 1 | 0.5 | 0.25 | 0.015 | N/T | N/T |
| *Mycoplasma gallisepticum* "R" | 0.125 | 0.125 | N/T | N/T | 0.5 | 0.03 |

N/T = Not Tested

Evaluation of antibiotics E19020 alpha and LL-E19020 beta for treating birds infected with *Clostridium perfringens*

TREATMENT MEANS

| | | | Lesion | % | Final | Feed/ |
|---|---|---|---|---|---|---|
| Treatment | Inf. | ppm | Scores | Mortality | Weight | Gain |
| Control | − | − | 0 | 0 | 643.3 | 1.83 |
| Control | + | − | 1.58 | 17.5 | 510.2 | 2.94 |
| E19020 alpha | + | 50 | 0.38 | 2.5 | 699.4 | 1.80 |
| E19020 alpha | + | 5 | 0.35 | 2.5 | 639.2 | 1.97 |
| E19020 beta | + | 50 | 0.37 | 2.5 | 628.8 | 1.78 |
| E19020 beta | + | 5 | 0.71 | 2.5 | 578.2 | 1.93 |

Inf = Infected

EXAMPLE 6

Evaluation of antibiotic LL-E19020α for treating *Mycoplasma gallisepticum* caused chronic respiratory disease in poultry This study is conducted to evaluate the efficacy of antibiotic LL-E19020α against *Mycoplasma gallisepticum* caused chronic respiratory disease in poultry. The antibiotic is fed continuously at 10 and 50 g/ton for 7 days pre- and 7 days postchallenge. Birds similarly fed a diet containing 100 g/ton chlortetracycline serve as a positive control group. Infected and noninfected, nonmedicated control groups are also included. After 7 days on respective treatment diets, birds are challenged with *M. gallisepticum* (MG) into the right and left post-thoracic air sacs. The air sacs are cultured for the presence of Mycoplasma from all birds dying postchallenge. The air sacs of all birds are scored based on gross lesions upon necropsy at death or at study end. Survivors at study end are bled prior to necropsy for *Mycoplasma gallisepticum* serology testing. Body weight and feed intake measurements are made at specified intervals during the study.

| Drug in Feed | Level (g/ton) | Mycoplasma Challenge | No. Replicate Cages | No. Birds Per Replicate | Total No. Birds Per Treatment |
|---|---|---|---|---|---|
| LL-E19020 alpha | 10 | Yes | 4 | 20 | 80 |
| LL-E19020 alpha | 50 | Yes | 4 | 20 | 80 |
| Chlortetracycline | 100 | Yes | 4 | 20 | 80 |
| None | 0 | Yes | 4 | 20 | 80 |
| None | 0 | No | 4 | 20 | 80 |

Clinical observations:
General clinical signs are noted for birds in each cage on each postchallenge day. Signs include respiratory rales, snicking and ruffled feathers.
Air sac lesion scoring:
Air sacs are scored as follows:
0 = normal, clean, no lesions
1 = slight cloudiness and thickening
2 = readily visible gray to yellow exudate and thickened
3 = severely exudative and thickened

| | Overall summary of performance and lesion data | | | |
|---|---|---|---|---|
| Treatment | Final Mean Body Weight (g) of Survivors | Overall Feed-to-Gain | Overall % Mortality | Mean Air Sac Lesion Scores |
| 1 10 g/ton LL-E19020 alpha | 336 | 1.88 | 41.3 | 2.04 |
| 2 50 g/ton LL-E19020 alpha | 349 | 1.84 | 36.3 | 2.11 |
| 5 100 g/ton Chlortetra-cycline | 398 | 1.83 | 25.0 | 1.88 |
| 6 Infected, Nonmedicated | 328 | 2.00 | 48.8 | 2.04 |
| 7 Noninfected, Nonmedicated | 464 | 1.80 | 00.0 | 0.00 |

From the above data it can be seen that *Mycoplasma gallisepticum* infected chicks receiving 50 grams of the antibiotic LL-E19020α per ton of feed had better weight gain, better feed to gain ratios and less mortality than infected nonmedicated chicks.

What is claimed is:

1. A method for treating necrotic enteritis, *Mycoplasma gallisepticum* caused chronic respiratory disease and fowl cholera in infected birds comprising orally administering to said infected birds a pharmaceutically effective amount of antibiotic LL-E19020α, LL-E19020β or a physiologically acceptable salt thereof.

2. A method according to claim 1, wherein said birds are poultry, game birds raised in captivity, avian pets or avian zoological specimens infected with *Clostridium perfringens, Mycoplasma gallisepticum* or *Pasturella multocida.*

3. A method according to claim 1 wherein the antibiotic is orally administered to said birds at concentrations of from 0.5 ppm to 1000 ppm in or with said birds feed or drinking water.

4. A method according to claim 1 wherein the infected birds are chickens or turkeys and the antibiotic is administered in a feed containing 1.0 ppm to 50 ppm of LL-E19020α, LL-E19020β or a physiologically acceptable salt thereof.

5. A method according to claim 1 wherein the infected birds are chickens or turkeys and the antibiotic is administered in drinking water containing 1.0 ppm to 50 ppm of LL-E19020α, LL-E19020β or a physiologically acceptable salt thereof.

6. A method for treating chickens or turkeys infected with necrotic enteritis comprising orally administering to said infected birds feed or drinking water containing 0.5 ppm to 1000 ppm of antibiotic LL-E19020α, LL-E19020β or a physiologically acceptable salt thereof.

7. A method for treating chickens or turkeys infected with *Mycoplasma gallisepticum* caused chronic respiratory disease comprising orally administering to said infected birds feed or drinking water containing 0.5 ppm to 1000 ppm of antibiotic LL-E19020α, LL-E19020β or a physiologically acceptable salt thereof.

8. A method for treating chickens or turkeys infected with fowl cholera comprising orally administering to said infected birds feed or drinking water containing 0.5 ppm to 1000 ppm of antibiotic LL-E19020α, LL-E19020β or a physiologically acceptable salt thereof.

* * * * *